(12) United States Patent
Travers et al.

(10) Patent No.: US 6,951,759 B2
(45) Date of Patent: Oct. 4, 2005

(54) DETECTION OF BACTERIAL VAGINOSIS

(75) Inventors: Paul James Travers, Chorlton (GB); Amjad Nissar Chaudry, Chorlton (GB); Andrew John Tummon, Middlewich (GB); Martin James Henery, Alderley Edge (GB)

(73) Assignee: Osmetech PLC, Crewe (GB)

( * ) Notice: Subject to any disclaimer, the term of this patent is extended or adjusted under 35 U.S.C. 154(b) by 325 days.

(21) Appl. No.: 10/219,939

(22) Filed: Aug. 14, 2002

(65) Prior Publication Data

US 2003/0044996 A1 Mar. 6, 2003

Related U.S. Application Data

(60) Provisional application No. 60/335,185, filed on Nov. 15, 2001.

(30) Foreign Application Priority Data

Aug. 17, 2001 (GB) .............................. 0120062

(51) Int. Cl.[7] .............................. G01N 33/00
(52) U.S. Cl. ................ 436/129; 436/111; 436/181; 436/811; 600/562; 435/252.1; 435/807
(58) Field of Search ................ 436/129, 111, 436/181, 811; 600/562; 435/252.1, 807

(56) References Cited

U.S. PATENT DOCUMENTS

| 5,425,869 A | 6/1995 | Noding et al. ............... 204/418 |
| 6,620,107 B2 * | 9/2003 | Payne et al. ................. 600/532 |

FOREIGN PATENT DOCUMENTS

| JP | 63255653 | 10/1988 | .......... G01N/27/30 |
| JP | 01074442 | 3/1989 | .......... G01N/27/30 |
| WO | WO 01/13087 A2 | 2/2001 | |

OTHER PUBLICATIONS

Brand et al., "Trimethylamine The Substance Mainly Responsible For the Fishy Odor Often Associated with Bacterial Vaginosis," Obstetrics & Gynecology, vol. 68, No. 5, pp. 682–685 (1986) (abstract).*
Hillier, Sharon L., "Diagnostic microbiology of bacterial vaginosis," Am. J. Obstet Gynecol, Aug. 1993, pp. 455–459.
Spiegel, Carol A., et al., "Anaerobic Bacteria in Nonspecific Vaginitis," The New England Journal of Medicine, vol. 303, No. 11, Sep. 11, 1980, pp 601–606.
Thomason, Jessica L, et al., "Is analysis of vaginal secretions for volatile organic acids to detect bacterial vaginosis of any diagnostic value?," Am. J. Obstet Gynecol, Dec. 1988, pp. 1509–1511.
Stanck, Ronald et al., "High Performance Ion Exclusion Chromatographic Characterization of the Vaginal Organic Acids in Women with Bacterial Vaginosis," Biomedical Chromatography, vol. 6, 1992, pp. 231–235.
Piot, P., et al., "The Vaginal Microbial Flora in the Non–Specific Vaginitis," Eur. J. Clin. Microbiol, vol. 1, No. 5, Oct. 1982, p. 301–306.
Ison, C.A., et al., "Non–volatile fatty acids in the diagnosis of non–specific vaginitis," J. Clin. Pathol., vol. 36, 1983, pp. 1367–1370.

(Continued)

Primary Examiner—Monique T. Cole
(74) Attorney, Agent, or Firm—Marger Johnson & McCollom, PC

(57) ABSTRACT

There is disclosed a method for detecting the presence of bacterial vaginosis in a female subject comprising the steps of:

obtaining a sample from the vaginal region of the subject;
detecting acetic acid present in the sample; and
correlating the presence of detected acetic acid with the presence of bacterial vaginosis.

16 Claims, 5 Drawing Sheets

OTHER PUBLICATIONS

Spiegel, Carol. A. et al, *Mobiluncus* gen. nov., *Mobiluncus curtisii* subsp. *curtisii* sp. nov., *Mobiluncus curtisii* subsp. *holmesii* subsp. nov., and *Mobiluncus mulieris* sp. no., Curved Rods from the Human Vagina, International Journal of Systematic Bacteriology, vol. 34, No. 2, Apr. 1984, pp. 177–184.

Crawley, B. A., et al., "C–82. Microbial Growth, Antibiotic Sensitivity Patterns and the Electronic Nose," Abstracts of the General Meeting of the American Society For Microbiology, vol. 99, 199, p. 121.

Chandiok, S., et al., "Screening for bacterial vaginosis: a novel application of artificial nose technology," J. Clin. Pathol., vol. 50, 1997, pp. 790–791.

Xu, Clarke X., et al., "Development of a diamine biosensor," Talanta, vol. 44, Jan. 1997, pp. 1625–1632.

Chandiok, S.; Crawley, B.A.; Oppenheim, B.A.; Chadwick, P.R.; Higgins, S. and Persaud, K.C., "Screening for bacterial vaginosis: a novel application of artificial nose technology," Short Reports, J. Clin Pathol 1997; 50:790–791.

\* cited by examiner (a)

(b)

DETECTION OF BACTERIAL VAGINOSIS

RELATED APPLICATION DATA

This application claims priority from Great Britain Application No. 0120062.5, filed 17 Aug. 2001 and U.S. Provisional Application Ser. No. 60/335,185, filed 15 Nov. 2001.

BACKGROUND OF THE INVENTION

This invention relates to the detection of bacterial vaginosis using a gas detector.

Bacterial vaginosis (EV) is a well known, but not well understood or well defined, condition which exhibits uncertain symptoms. Numerous reports cite as much as 50% of the affected population being asymptomatic. The remaining 50% of the population either go undetected or present during routine examination for an associated or uncorrelated problem.

Originally thought to be a benign infection recent studies have linked the problem to increased risk of intra-amniotic infection, choroamionitis, post-caesarean and post-partum endometritis, adverse pregnancy outcome, pre-term labour and birth, premature rupture of membranes at term and post-hysterectomy cuff cellulitis.

BV is commonly thought to arise as a result of fluctuation of the normal vaginal flora, In some cases the flora can fluctuate naturally over the menstrual cycle with no adverse effects. It is thought that one of the primary controlling mechanisms controlling BV causative bacteria is the presence of adequate colonies of *Lactobacillus* sp. that produce hydrogen peroxide. The most common organisms associated with BV are: *Gardnerella vaginalis, Bacteroides* (*Prevotella*) spp., *Mobiuncus* spp. and *Mycoplasma hominis*. However, the presence or absence of these flora is not reliably diagnostic.

Treatment after a correct diagnosis is usually quite effective and usually comprises of treatment with oral doses of metronidazole. Topical treatments with metronidazole or clindamycin are also common. However, in Doctors' surgeries it is not uncommon for general practitioners (GPs) to wrongly diagnose vaginal infections, e.g., some cases of *Candida* are diagnosed as BV and vice versa. A distinction between a yeast and bacterial infection is important, as non-specific antibiotics can cause more problems for the sufferer. For symptomatic patients, BV has an incidence of 40% compared with *Candida* and *Trichomonas*. A swift, preferably in-situ, diagnosis would enable immediate correct therapy (usually comprising antibiotics in the case of DV) to be administered. In GPs' surgeres, a means of differentiating a bacterial infection from a yeast infection would enable the correct type of treatment to be prescribed.

In fact, the consequences of BV are wide and varied and are not completely understood. This is perhaps unsurprising given the difficulties in getting reliable BV data for a population. The primary challenge facing any prospective diagnostic technique (or aid to diagnosis) is finding a unique indicator against which BV may be detected. Currently the Amsel test is the benchmark for determining the problem. The criteria for the test rely on at least three out of four conditions being met. These are;

pH of vaginal fluid >4.5

Typical thin, homogenous vaginal discharge

Release of strong fishy smell on adding alkali (10% KOH) to a sample of vaginal fluid (whiff test), Clue cells present on microscopic examination of a wet mount of vaginal fluid.

It should be noted that the presence of trimethylamine (TMA) in some BV samples is undisputed, and TMA is often cited as being the volatile associated with the unpleasant fishy odour referred to above.

Individually none of these tests are diagnostic. pH variation of the vaginal fluid is nearly always present in BV positive patients but it is a non-specific. test and the variation is equally likely to be caused by another infection or problem. Additionally, contamination of the sample by cervical mucus (typical pH 7) can lead to false diagnoses in some cases. pH variation also occurs as part of the natural menstrual cycle. Ethnic background is also a factor affecting vaginal pH and his has been postulated as a reason for the relatively higher number of black American women who present with the disease. According to Hay, pH is highly sensitive (97%) but very non-specific giving false positives in 47% of cases. Conversely, discharge is very accurately recognised by clinicians giving false positives at 3% but only has a specificity of 67%. Following this, the "whiff" test also gives low false positives (1%) but is non-specific (43%). Finally clue cells are typically found in 81% of positive BV cases whilst 6% of non-BV cases have positive clue cell tests. Other trials report variation on these figures but all concur with the non-specificity and reliability of any one individual test.

It is known from the applicant's International Application No. WO 95/33848 that microorganisms can be detected using arrays of gas sensors to detect characteristic gases or vapours produced by the microorganisms. An example of such an array is an array of semiconducting organic polymer gas sensors. The applicant's International Applications Nos. WO 98/29563 and WO 98/39470 describe further aspects and refinements to the technique, and related developments. In general, the approach with arrays of gas sensors is to utilise a large number (twenty, thirty or more) of different gas sensors which possesses different but overlapping sensitivities towards different gaseous species (so-called "electronic noses"). Oases are recognised from the characteristic "fingerprint" or pattern of response across the array. However, detection can be difficult in a complex system having mixed populations of microflora and microfaunae and/or systems in which many volatile species are present.

Of the particular relevance to the present application are International Application number WO 94/04916 and Chandiok et al (S. Chandiok, B A Crawley, B A Oppenhein, P R Chadwick, S Higgins, and K C Persaud, Journal of Clinical Pathology, 50 (1997) 790). Both documents describe attempts to detect BV using arrays of semiconducting organic polymers, and in both cases it is believed that the gaseous species detected were ammonia and/or TMA. In fact, WO 94/04916 specifically describes a process rather similar to the whiff test discussed above, in which KOH is added to a sample, thereby releasing volatile alkaline species into the gas phase. It should be noted, when considering the present invention as described below, that the sensors used in the investigation of Chandiok et al are not sensitive to fatty acids such as acetic acid.

SUMMARY OF THE INVENTION

The present invention overcomes the above-mentioned problems and difficulties, and provides a quick, reliable and practical screening technique for the detection of bacterial vaginosis. The technique is easily automated and may be performed by unskilled operatives with a minimum of technical back-up.

For the avoidance of doubt, the terms "gas" and "gases" are understood to embrace all species present in the gas phase, including volatile species emanating from liquids and sublimed species emanating from solids.

According to a first aspect of the invention there is provided a method for detecting the presence of bacterial vaginosis in a female subject comprising the steps of:

obtaining a sample from the vaginal region of the subject;

detecting acetic acid present in the sample; and correlating the presence of the detected acetic acid with the presence of bacterial vaginosis.

Surprisingly, acetic acid has been found to be a "marker" species indicative of BV, and has enabled the provision of a detection technique having the aforesaid advantages.

In a preferred embodiment, acetic acid present as a gas in a headspace associated with the sample is detected using a detector which is sensitive to the presence of acetic acid.

The sample may be a swab sample, and a high vaginal swab sample maybe obtained. A high vaginal swab is a swab taken from the Posterior Formix, any of the three vaulted spaces at the top of the vagina, or from around the cervix of the uterus. Thus, the sample can be "indirect", in the sense that the sample comprises an object which is physically removed from the vaginal region of the subject to a sampling portion of the detector. Alternatively, it may be possible to sample gases directly from the vaginal region of the subject using the detector: this alternative is also within the scope of the invention.

Ammonia and, optionally, amine species (such as TMA) present in the sample maybe detected, and the presence of acetic acid, ammonia and, optionally, amine species maybe correlated with the presence of bacterial vaginosis. Preferably, ammonia and, optionally, amine species present as gas in the headspace associated with the sample are detected by the detector.

The detector may comprise semiconducting organic polymer.

The detector may comprise an array of gas sensors. An array, in the context of the present invention, is two or more gas sensors. In contrast to conventional electronic noses, it has been found that arrays having only a small number of physically different gas sensors can be used advantageously, For example, an array may comprise five or fewer sensor types which are sensitive to acetic acid, and five or fewer sensor types which are sensitive to ammonia (and/or amines). As few as four different sensor types have been found to be sufficient. It may be possible to use a single acetic acid sensitive gas sensor in place of an array.

The array may comprise gas sensors having semiconducting organic polymer as a gas sensitive layer.

The detector may comprise at least one conductimetnic gas sensor having a gas sensitive layer onto which gases absorb and desorb, and in which analytes are detected by:

exposing the gas sensor to the headspace, thereby allowing the adsorption of analytes present in the headspace onto the gas sensitive layer; and making conductimetric measurements of the sensor during a desorption phase in which there is nett desorption of analyte from the gas sensitive layer. This approach has been found to be extremely advantageous in terms of improving sensitivity and reproducibility. The principal reason for this is that the effect of water vapour appears to be substantially eliminated in the desorption phase. This is a considerable advantage, and significantly enhances the detection of fatty acids, ammonia and amines. However, it will be appreciated that this approach is not limited to the detection of these species, and nor is it limited to the method of the present invention. Rather, the approach of making conductimetric measurements in the desorption phase can be employed as a general technique for detecting analytes using conductimetric gas sensors which have a gas sensitive layer. Typically, a pulse of gas from the headspace is flowed over the sensor, and the desorption phase commences once this pulse of gas has finished flowing over the sensor. The technique of making conductimetric measurements in the desorption phase works best when analytes of interest have significantly longer desorption times than water.

The conductimetric gas sensor or sensors may comprise semiconducting organic polymer.

This method may further comprise the steps of:

performing a data reduction of one or more measurements of one or more calibration samples to provide reference scores and reference loadings; and performing data reduction of the output of the detector using the reference loadings.

In a preferred embodiment the data reduction comprises a principal components analysis (PCA). Other forms of data reduction, such as Sammon mapping, maybe feasible.

This approach permits very convenient and quick assessment of whether a sample is infected on the basis of simple assessment criteria. Furthermore, it is possible to calibrate the system and to perform self-test protocols using its approach.

The reference scores and reference loadings may relate to a co-ordinate system having an axis which is correlated to the presence of acetic acid. The reference scores and reference loadings may relate to a co-ordinate system having one axis which is correlated to the presence of acetic acid and another axis which is, correlated to the presence of ammonia and, optionally, amine species.

The method may be one in which:

the reference scores and reference loadings relate to a co-ordinate system having a species characteristic axis which is correlated to the presence of a species; and data reduction of intensity data from the detector is performed using the reference loadings so that position along the species characteristic axis is related to the concentration in the headspace of the species which is correlated to the species characteristic axis. In this way the intensity data can be related to the concentration of marker species which in turn can be related to the number of infecting organisms. In particular, it is possible to observe if a threshold concentration has been crossed, allowing the correlation of detector output with the presence of infection to be made. It should be noted that in the prior art, intensity data from electronic noses comprising arrays of gas sensors are usually removed by normalisation before analysis such as PCA, so that concentration independent "fingerprints" can he obtained.

According to a second aspect of the invention there is provided a gas sensing system adapted to detect the presence of bacterial vaginosis in a female subject by the method of the first aspect of the invention comprising:

a detector which is sensitive to the presence of gaseous acetic acid and adapted to sample a headspace associated with the sample; and analysis means for analysing the output of the detector and correlating the presence of detected acetic acid with the presence of bacterial vaginosis.

The analysis means may correlate the presence of acetic acid, ammonia and, optionally, amine species with the presence of bacterial vaginosis.

Methods and apparatus in accordance with the invention will now be described with reference to the accompanying drawings, in which:

DETAILED DESCRIPTION

Figure 1:
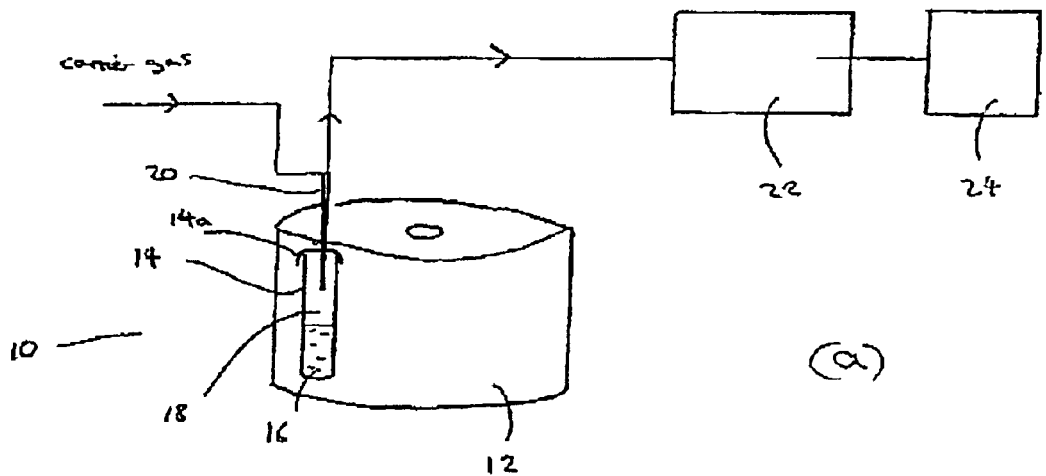
FIG. 1 shows (a) a schematic diagram of apparatus suitable for identifying the presence of BV and (b) Sampling of a headspace.
Figure 1:
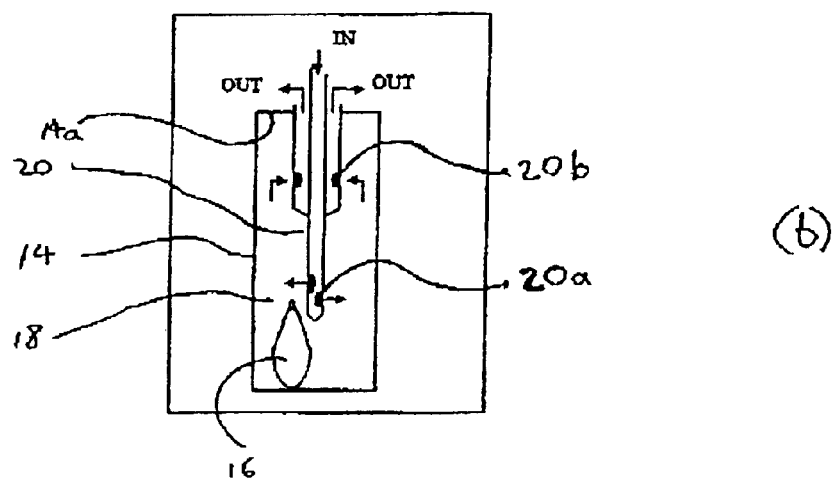

FIG. 1(a) schematically depicts apparatus shown generally at 10, for use with the method of the present invention. The apparatus comprises a sample carousel 12 in which a number of sample vials can be mounted and maintained at a constant temperature, for example 40° C. For simplicity, a single sample vial 14 is shown in FIG. 1(a). The vial 14 contains a sample 16 such as a swab taken from the vagina of a subject. Above the sample 16 is a gaseous headspace 18 which contains inter alia volatile species emanating from the sample 16.

The vial 14 has a septum 14a thereon which is pierced by a needle 20, the insertion of needle 20 into the vial 14 being performed automatically by the apparatus 10. The needle 20 is shown in more detail in FIG. 1(b). The needle 20 is of co-axial design, which permits a carrier gas (such as air, nitrogen or a noble gas) to be introduced to vial 14 via the inner lumen 20a of the needle 20. Gases in the headspace 18 are entrained in tile flow of carrier gas, which exits the vial 14 via the outer lumen 20b of the needle 20, and thereafter is flowed across a gas sensor array 22. In this way, the headspace 18 is sampled by a gas detector 22, which in this embodiment is a gas sensor array. It will be appreciated by the skilled reader that there are many other ways in which the headspace might be coupled to a gas detector. It may be possible to directly sample gases from the vaginal region of a subject using a suitable arrangement, such as a sampling probe coupled to the gas detector. Additionally, the use of devices such as filters and preconcentrators is feasible.

The gas sensor array 22 is selected so that it can detect acetic acid. This species can been found to constitute a "marker" species which can be indicative of BV infection. Other species can be detected in order to augment the identification. Ammonia and amine species such as TMA can be detected for this purpose. It is possible that further "marker" species might be detected in addition to acetic acid.

The output of the gas sensor array 22 is monitored and analysed by control means 24 which comprise computer means or other microprocessor-based analysis means. The control means 24 can also control the operation of the carousel 12, the flow of carrier gas, washing and calibration procedures, and the manner in which the gas sensor array 22 is operated or interrogated. However, it is quite possible to transfer data from the control means 24 to, for example, a remote computer for analysis. In any event, some form of analysis means is provided which is adapted to correlate the presence of the detected acetic acid with the presence of the infection. In this way, the sample 14 is screened for BV infection.

The method of the present invention has been used to screen samples for BV infection. The human vagina is a host to many species of microorganisms, and the headspace associated with a vaginal sample is itself complex. It is known from WO 95/33848 that microorganisms can produce volatile species which are characteristic of the microorganisms. What is not known from WO 95/33848 is how, with a highly complex headspace associated with a vaginal sample, one can identify the presence of BV infection from gases emanating from the sample. Furthermore, WO 94/04916 and Chandiok et al. are concerned with the detection of alkaline species such as ammonia and amines. The present invention overturns this conventional wisdom.

The pH of the sample can be lowered, by the addition of an acid in order to release acetic acid into the gaseous phase. However, it has been found that typically quite large concentrations of acetic acid are associated with positive BV samples (often at concentrations of 500 ppm or greater) and therefore acidification is not an essential element of the invention.

Optionally, a salt such as $Na_2SO_4$ can be added in order to displace less soluable volatiles, in particular organic species, from solution and into the gaseous phase. Backwashing between samples is advisable to prevent cross-contamination.

In a preferred embodiment, the gas detector is an array of gas sensors, and in a particularly preferred embodiment the gas sensors comprise semiconducting organic polymer gas sensors. However, in principle, other forms of gas detector might be employed, provided that they are sensitive to the marker species described above. Gas detection techniques which are candidates for use in the present invention include gas chromatography, mass spectrometry and spectroscopic techniques such as IR spectroscopy. Other forms of gas sensor array might be contemplated, such as arrays of metal oxide sensors, SAW sensors, quartz resonators, "composite" sensors of the type described generally in U.S. Pat. No. 5,571,401, and arrays comprising mixtures thereof.

Embodiments of a preferred—but non-limiting-kind of gas detector will now be described, namely arrays of semiconducting organic polymer gas sensors. As discussed above, the traditional approach with such arrays is to employ a large number (typically twenty or more) of different sensors having different polymers and/or different dopant counterions, thus producing an array in which the individual gas sensors exhibit broad and overlapping sensitivities towards a range of different gases. The same principle applies to other arrays of gas sensors, such as metal oxide sensors. Devices of this type are commonly referred to as "electronic noses".

In direct contrast, it has been found that screening for infection according to the present invention can be advantageously performed using an array which comprises a limited number of sensor types, ie. sensors with physically different polymer/counterion combinations. In one example, four types of selective conducting polymer sensors have been developed and incorporated into a device. Two of these are acid sensitive, one sensitive to ammonia, and the other sensitive to ammonia and trimethyl amine. These four sensor types are incorporated into a 48 sensor array, comprising 12 sets of replicate sensors. The provision of 12 replicates of each sensor type permits signal averaging over a large number of sensors. Additionally, sets of replicate sensors allows the array to function in the event that one or even more than one sensor in any given replicate set malfunctions. Fewer sensors still might be utilised, particularly if acetic acid alone is detected as a "marker".

The changes in resistance of each sensor type in response to a volatile sample are recorded with time, and are averaged for each sensor type over the array. It has been observed that it is possible to eliminate the effect of water vapour on the response of the sensors by choosing a portion of the trace corresponding to the desorption phase of the experiment. With acetic acid as the analyte, it has been observed that there is undershoot in the signal below the previous baseline (see FIG. 2a). This effect is reproducible is a function of concentration of acetic acid, and is a parameter due to the type of materials incorporated into the sensor. The time course is primarily dependent on the sensor kinetics, but carrier flow and header geometry will also have an effect.

Figure 2:
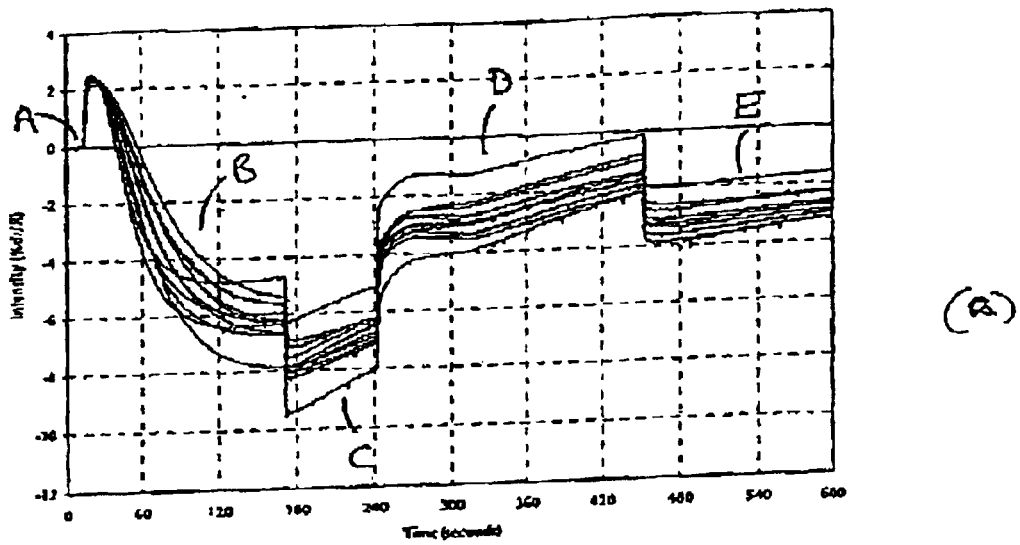
FIG. 2 shows typical sensor responses a) to acetic acid of one polymer type and b) to ammonia of another polymer type as a function of time.
Figure 2:
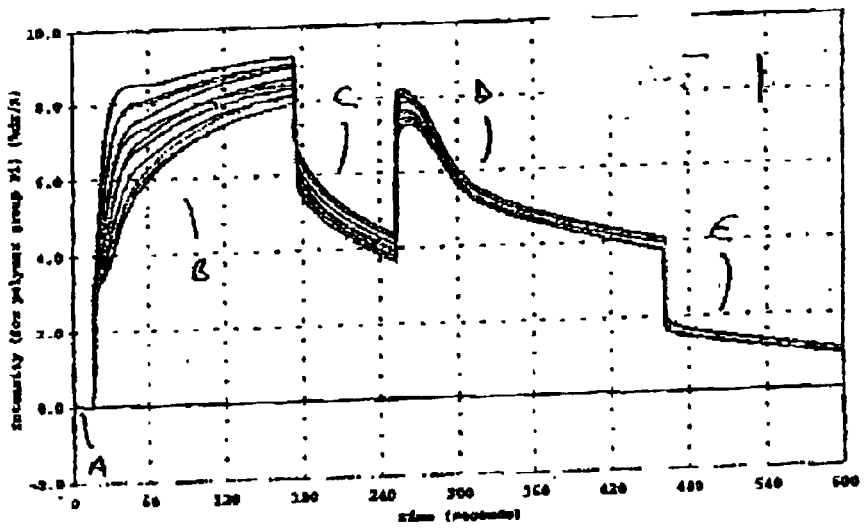

FIG. 2a shows a number of response profiles to acetic acid for a semiconducting organic polymer sensor against time. The baseline response is indicated at "A". During the period of time indicated as "B", the sensors are exposed to a pulse of gas comprising acetic acid entrained in a carrier gas. This can be regarded as an "adsorption phase" during which there is nett adsorption of acetic acid—and water—onto the sensors. After the gas pulse has finished, there is a desorption phase, or recovery phase, which is indicated as "C", during which there is a nett desorption of analyte from the sensors.

It can be seen that the response becomes negative with respect to the baseline during the recovery phase. With fatty acid analytes, signal averaged over the period C is a function of the concentration of acid present in the headspace. The responses shown at "D" and "E" relate to (standard) wash and reference cycles, respectively.

It should be noted that generally similar responses are obtained when the sensors are exposed to ammonia (FIG. 2b), ie. there are distinct baseline, adsorption and recovery phases. However, the response in the recovery phase in this instance remains positive with respect to the baseline. Measurements made during the recovery phase are also substantially free from interferences from moisture.

Interference from moisture is a major limitation for a number of gas sensing technologies which interrogate a gas sensitive layer of some kind upon which analytes—and water vapour—can reversibly adsorb. Semiconducting organic polymers are an example of such a gas sensitive layer. The above described technique for rejecting interfering signals due to moisture is of broad significance—not only is the technique applicable in the context of screening for BV infection, it can be utilised more widely in the detection of analytes per se.

It is believed that the displacement of the sensor response from the baseline during the recovery phase is a result of the analyte still being bound at the polymer surface. As a result of interactions between the bound analyte and the electronic structure of the polymer, the polymer can be more doped (producing a negative response) or less doped (producing a positive response) than when the baseline measurements were made. It is believed that water desorbs from the polymer surface very rapidly during the recovery phase, and so most of the recovery phase is substantially moisture free. However, these mechanisms are speculative in nature, and should not be regarded as a limiting one.

It should be noted that analysis of the sensor response is not restricted to the recovery phase. In an alternative configuration the resistances recorded when the sensors are exposed to the headspace from the sample (ie, the sample phase) could be compared to the resistances recorded for an equivalent exposure to a threshold standard. By determining whether he sample resistance lies above or below the resistance values for the threshold standard the BV diagnosis can be made. In this configuration the calibration requirements for the system may be greatly reduced.

It should be noted that, whilst prior art semiconducting organic polymer gas sensors generally show good sensitivity towards ammonia, it has not previously been possible to detect fatty acids such as acetic acid at low concentrations using such gas sensors. The present invention provides new gas sensors which employ new semiconducting organic polymers With these polymers, high sensitivity towards fatty acids (such as acetic acid) and ammonia can be achieved.

The new materials have a bilayer structure with a baselayer of polypyrrole deposited chemically using ferric chloride as an oxidant. Different sensor types are manufactured by electroechemically depositing different top layer polymers onto this baselayer. The four types of sensors incorporated into the device described above use the following monomer/electrolyte combinations for the electrochemical deposition stage:

1. 3-Hexanoylpyrrole/tetraethylammonium p-toluenesulponate
2. 1-Octylpyrrole/tetrabutylammonium triflate
3. 3-Dodecylpyrrole/tetraethylammonium tetrafluoroborate
4. 1-Dodecylpyrrole/tetraethylanmmoniun tetrafluoroborate The 3-substituted monomers can be synthesised following the method of Ruhe et al (Makromol, Chem., Rapid Commun. 10 (1989) 103). The 1-substituted monomers can be synthesied following the method of Santaniello et al (Synthesis, 1979, 617).

Further details of the polymerisation conditions and of the preparation of polymer bilayers having a baselayer of polypyrrole can be found in the Applicant's earlier International Publication WO 96/00383.

In a typical procedure, the sample is equilibrated at 40° C. for ca. 3 minutes prior to sampling to allow a consistent generation of the sample headspace. Nitrogen gas is humidified to 50% relative humidity and introduced into the sample vial directly above the surface of the swab. The sample headspace is delivered to the sensor array for 3 minutes at a flow rate of ca. 60 mlmin$^{-1}$. The sensor array is allowed to recover for a few minutes before a "wash" gas, preferably a high concentration acetic acid wash, is passed over the sensor typically for 1 to 4 minutes.

Data Processing

An object of the invention is to produce a rapid screening system for BV. The embodiment described below utilises the acetic acid, ammonia and TMA sensitive sensor array described above and is capable of making a decision based on the relative intensities of acetic acid and/or ammonia and TMA present in the headspace. Analysis of the sensor array has been greatly facilitated by a novel data processing technique which is discussed below and which is based on principal components analysis (PCA—see, for example, J E Jackson, J Qual. Tech., 13(1) (1981)). It has been established that if a principal components analysis of the intensity data from the highly ortogonal sensors is carried out, the distribution of points projected on a first principal components axis PC 1 is correlated to acetic acid, and that the points projected on a second principal components axis PC 2 are correlated to ammonia. The distribution along either coordinate axis is also a function of the concentration of the analyte in the headspace, and hence of the concentration of marker chemicals produced by the microorganisms present in the sample. Thus it is possible to utilise a thresholding technique for deciding whether or not a sample is positive or negative, based on user-defined clinical criteria. In broad terms, the data processing comprises using calibration samples to establish a PCA "calibration map", and then projecting data obtained from enclosed samples onto this PCA calibration map in order to establish if these data are indicative of infection.

Data processing is described in more detail below, with reference to various calibration and measurement process which are performed.

1. Calibration

Calibration involves running calibration standards to generate a reference map, verifying results and storing PCA loadings information.

In one example the array is calibrated using defined standards consisting of a "blank" sample, two acetic acid standards of different concentrations, and ammonium hydroxide. Typically, the calibration process is accompanied by repeatability checks on the standards in order to verify tat there is sufficient discrimination between standards and that repeatability is within acceptable bounds. 1 ml sample volumes are used as above. As part of each experimental run, subsets of standards are run, each sample cycle lasting 20 minutes. In preferred, but non-limiting, embodiments, the blank is water, one acetic acid standard comprises 900 ppm acetic acid in 0.01M HCl, the other acetic acid standard is 5000 ppm acetic acid in 0.01M HCl, and the ammonium hydroxide standard is 10 ppm in 0.01 M NaOH. The subset of standards can be used to confirm that the performance of the system is still the same as during its calibration and hence that the samples can be processed.

1.a. Calibration Map

Figure 3:
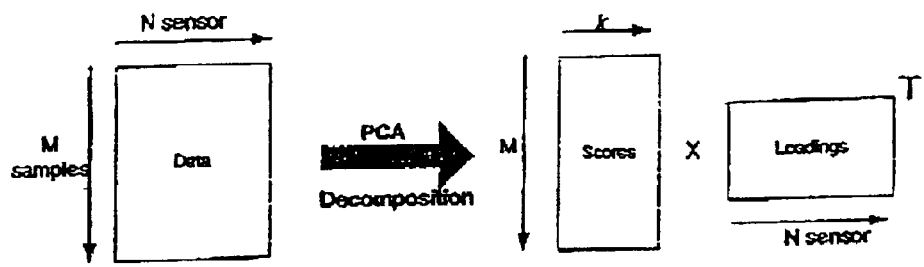
FIG. 3 shows a PCA transformation.
Figure 4:
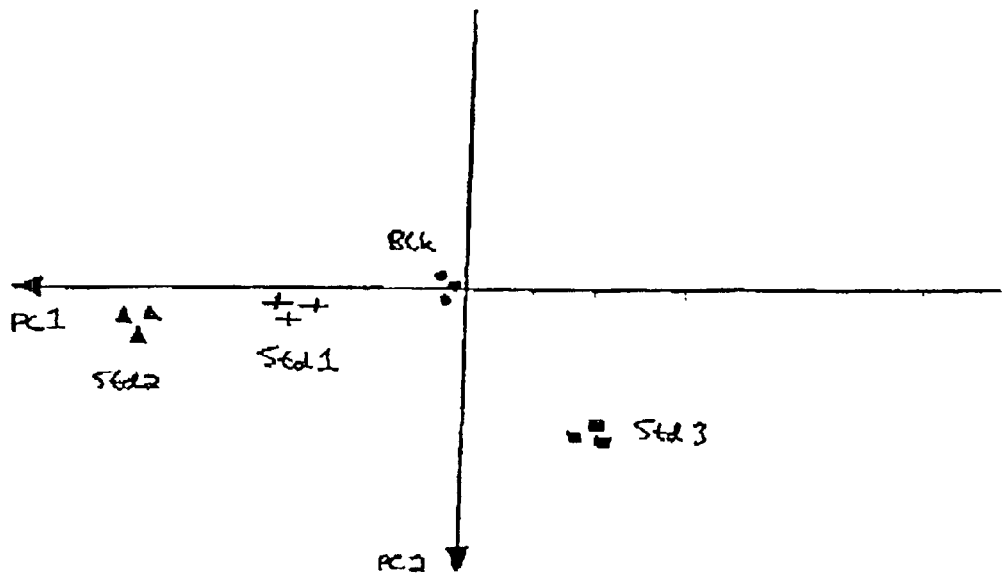
FIG. 4 shows a PCA calibration map.

The calibration data is transformed using Principal Component Analysis (PCA) to characterise the instrument sensor responses for the calibrants run, thus defining a two-dimensional mapping space on to which all subsequent samples analysed can be projected. PCA decomposes the original calibrant data matrix into a set of scores and loading vectors, in which scores contain information of how samples relate to one another whilst the loadings show how variables relate to one another. This process is depicted in FIG. 3, and can be written as:

$$X = t \times p^T$$

where t denotes the scores, which are vectors of linear combinations of sensor variables that describe the major trends in the original data matrix X. The loadings, which are represented by p, are a set of orthonormal eigenvectors representing a new set of axes onto which the scores information is projected. In FIG. 3 T denotes the transpose of a matrix. The result is a "calibration map" which is shown in FIG. 4.

Figure 5:
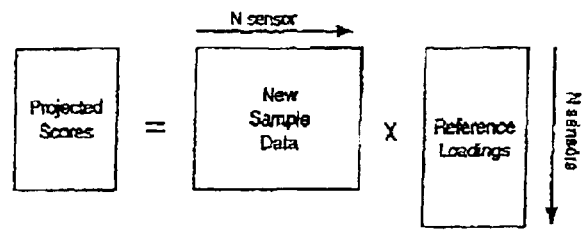
FIG. 5 shows the calculation of projected PCA scores.

Projected scores (PC1 and PC2) can be calculated by multiplying the analysis results with the reference loadings calculated in the calibration step. This process is depicted in FIG. 5.

1.b. Setting Thresholds

In the following discussion, Blk is the water standard referred to above, Std1 is the lower concentration acetic acid standard, Std2 is the higher concentration Where A,B,C,D,E and F are constant terms the values of which are determined by the parameters (r, s', c, d, M($\theta_r$), N($\theta_r$)) such that:

$$A = s'^2 M^2 + r^2 N^2$$

$$B = s'^2 N^2 + r^2 M^2$$

$$C = -2(s'^2 Mc + r^2 Nd)$$

$$D = 2(s'^2 Nc - r^2 Md)$$

$$E = -2(s'^2 MN - r^2 MN)$$

$$F = s'^2 c^2 + r^2 d^2 - r^2 s'^2$$

The parameters M($\theta_r$) and N($\theta_r$) are defined below and are dependent on $\theta_r$.

Figure 6:
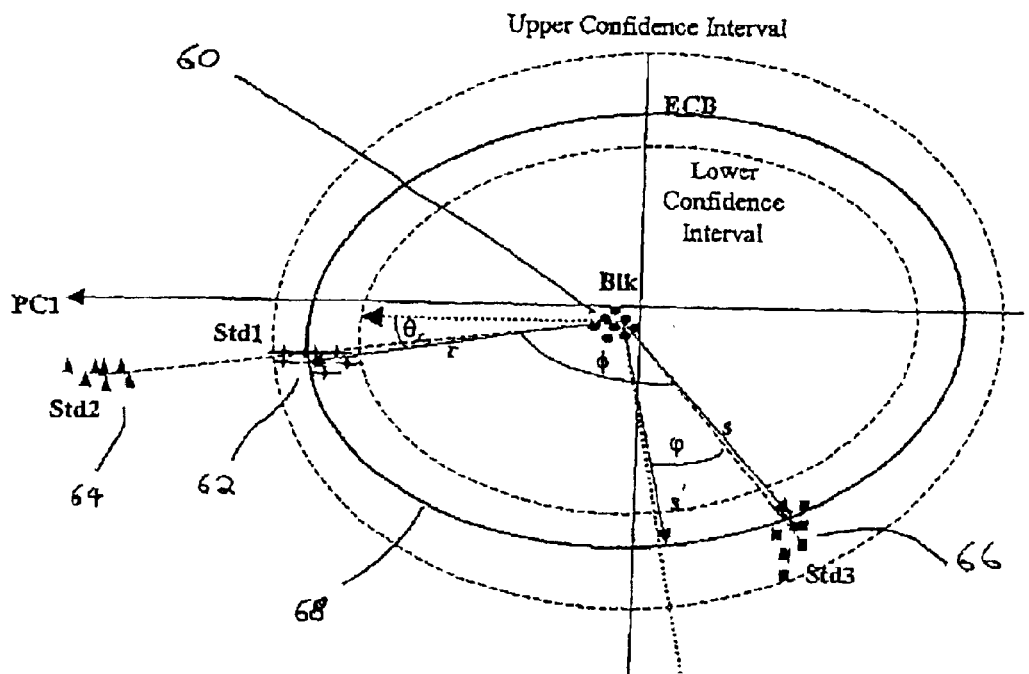
FIG. 6 is a graphical representation of ellipses projected onto the PCA calibration map.

The five parameters r, s', c, d, $\theta_r$ can be determined from the set of calibration data. FIG. 6 shows the two dimensional PCA reference map with the Blk 60, Std1 62, Std2 64 and Std3 66 calibration data projected thereon. FIG. 6 also depicts the parameters r, s and $\theta_r$ and the resultant ellipse 68.

Each calibration sample is defined by a score (t1, t2) value along each principal component axes PC1 and PC2, while ($\overline{t1}_x$, $\overline{t2}_x$) denotes the mean score for a of n-repeats of a chemical standard X. The length s' is the resolved distance (between the mean scores for Std3 and the mean scores for Blk) orthogonal to vector P determined by vector $\vec{s}$ which is at an angle φ to vector $\vec{r}$.

The five parameters r, s', c, d, $\theta_r$ are calculated as follows:

Angle of Rotation θacetic acid standard referred to above, and Std3 is the ammonium hydroxide standard referred to above. Std1 and Std3 correspond to the threshold concentrations of acetic acid and ammonium, respectively, above which infection is considered to be present.

It is possible to set threshold levels which, if exceeded, are taken to be indicative of infection. A relatively straightforward way of doing this is to define a threshold PC1 value and a threshold PC2 value. However, the present invention provides an improved thresholding technique which generates an ellipse, and utilises the boundaries of the generated ellipse as a threshold. An advantage with the use of an ellipse for this purpose is that the effects of sensor drift, which inevitably occurs over a period of time, can be taken into account.

An ellipse is defined by the five parameters, r, s', c, d, $\theta_r$, where:

r is the radius of the major axis s' is the radius of the minor axis c and d relate to the coordinates of the centre of the ellipse and $\theta_r$ is the angle of rotation between the positive x axis, and the axis radii established by Std1.

More specifically, an ellipse can be expressed algebraically in the form:

$$Ax^2 + By^2 + Cx + Dy + Exy + F = 0$$

From FIG. 6 the angle θ is defined as;

$$\theta_r = \left| \tan^{-1}\left( \frac{\overline{t2}_{Std1} - \overline{t2}_{Blk}}{\overline{t1}_{Std1} - \overline{t1}_{Blk}} \right) \right| \quad (1)$$

which is calculated in radians.

Parameters c and d (a Function of the Blk Centre)

The mean score of tie Blk ($\overline{t1}_{Blk}$, $\overline{t2}_{Blk}$) standards defines the centre of the ellipse The parameters c and d which are functions of both $\overline{t1}_{Blk}$ and $\overline{t2}_{Blk}$ are calculated as follows:

$$\begin{bmatrix} c \\ d \end{bmatrix} = \begin{bmatrix} \cos(-\theta_r) & -\sin(-\theta_r) \\ \sin(-\theta_r) & \cos(-\theta_r) \end{bmatrix} \times \begin{bmatrix} \overline{t1}_{Blk} \\ \overline{t2}_{Blk} \end{bmatrix} \quad (2)$$

Axis Radii (r)

The length r is calculated as follows.

$$r = \sqrt{(\overline{t1}_{Std1} - \overline{t1}_{Blk})^2 + (\overline{t2}_{Std1} - \overline{t2}_{Blk})^2} \quad (3)$$

where r is the Euclidean distance separation between the mean scores for std1 ($\overline{t1}_{Std1}$, $\overline{t2}_{Std1}$) and mean scores Blk ($\overline{t1}_{Blk}$, $\overline{t2}_{Blk}$).

Axis Radii (s')

The general equation of an ellipse centred at ($\overline{t1}_{Blk}$, $\overline{t2}_{Blk}$) with axis radii (r, s') rotated at an angle $\theta_r$ from the positive x-axis can be written as follows:

$$\frac{(Mx - Ny - c)^2}{r^2} + \frac{(Nx + My - d)^2}{(s')^2} = 1 \quad (4)$$

Where:

$M = \cos(-\theta_r)$ $N = \sin(-\theta_r)$ x = x-coordinate lying on the ellipse
y = y-coordinate lying on the ellipse By re-arranging equation (4) the length of s' can be determined for known values of c, d, r, $\theta_r$ and a point lying on the boundary of the ellipse. The (x,y) coordinates in equation (4) are defined by the mean score of Std3 ($\overline{t1}_{Std3}$, $\overline{t2}_{Std3}$) such that:

$$s' = \sqrt{\frac{r^2(N\overline{t1}_{Std3} + M\overline{t2}_{Std3} - d)^2}{r^2 - (M\overline{t1}_{Std3} - N\overline{t2}_{Std3} - c)^2}} \quad (5)$$

In general, a number of calibration measurements are made, and some variation is the recorded responses is observed. This data scatter is depicted in FIG. 6. It is possible to account for this variation in the recorded responses for the calibration standards by calculating a confidence band around the ellipse. To achieve this the variability $sd_r$ and $sd_s$ along the response vectors $\vec{r}$ and $\vec{s}$ for the axis radii parameters are calculated.

Calculation of $sd_r$ and $sd_s$ along $\vec{r}$ and $\vec{s}$ for the axis radii parameters.

Figure 7:
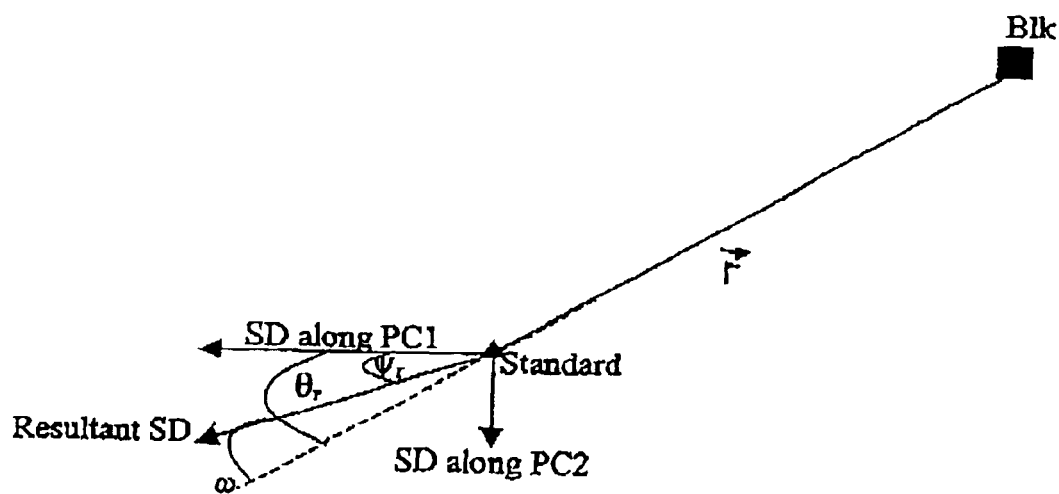
FIG. 7 is a graphical representation of the resolution of sample standard deviation along the PC1–PC2 axes.

A standard deviation value can be calculated for each standard Std1, Std3 along each component axis. This can be resolved as shown in FIG. 7 below to provide an estimate for the standard deviation (sd) along the vector component $\vec{r}$ and $\vec{s}$.

The resultant sd ($\kappa_r$) along $\vec{r}$ (Std1) is:

$$\kappa_r = \sqrt{sd_{t1}^2 + sd_{t2}^2} \quad (6a)$$

and the resultant sd ($\kappa_s$) along $\vec{s}$ (Std3) is:

$$\kappa_s = \sqrt{sd_{t1}^2 + sd_{t2}^2} \quad (6b)$$

Where $sd_{r1}$ is SD along PC1 and $sd_{r2}$ is SD along PC2.

The standard deviation along vector $\vec{r}$ (or $\vec{s}$) is given by:

$$sd_r = \kappa_r \times \cos(|\theta_r - \psi_r|) \tag{7a}$$

$$sd_s = \kappa_s \times \cos(|\theta_s - \psi_s|) \tag{7b}$$

where:

$$\theta_r = \left| \tan^{-1}\left( \frac{\overline{t2}_{Std1} - \overline{t2}_{Blk}}{\overline{t1}_{Std1} - \overline{t1}_{Blk}} \right) \right|$$

$$\psi_r = \tan^{-1}\left( \frac{sd2_{Std1}}{sd1_{Std1}} \right)$$

$$\theta_s = \left| \tan^{-1}\left( \frac{\overline{t2}_{Std3} - \overline{t2}_{Blk}}{\overline{t1}_{Std3} - \overline{t1}_{Blk}} \right) \right|$$

$$\psi_s = \tan^{-1}\left( \frac{sd2_{Std3}}{sd1_{Std3}} \right)$$

Having established $sd_r$ and $sd_s$ along the response vectors $\vec{r}$ and $\vec{s}$, the upper and lower lengths for $\vec{r}$ and $\vec{s}$ can be calculated at the desired confidence level such that:

$$(Ur, Lr) = r \pm t_{\alpha(2)\nu}(sd_r/\sqrt{n_r}) \tag{8}$$

$$(Us, Ls) = s \pm t_{\alpha(2)\nu}(sd_s/\sqrt{n_s}) \tag{9}$$

The confidence level ($\alpha$) is calculated for two-tailed t-statistic for $\nu$ degrees of freedom, where $\nu = n-1$ for n-repeats of each standard calibrant.

Before the equations for the upper and lower confidence bands can be established the coordinates for the lens Us and Ls are determined.

Calculating the PC scores for a point lying along the vector $\vec{s}$ whose length is Us and Ls from the ellipse centre.

Vector $\vec{s}$ can be written as:

$$\vec{s} = a\underline{i} + b\underline{j} \tag{10}$$

Where $$a = \overline{t1}_{Std3} - \overline{t1}_{Blk}$$

$$b = \overline{t2}_{Std3} - \overline{t2}_{Blk}$$

The length of s is given below:

$$|\vec{s}| = \sqrt{a^2 + b^2}$$

The PC scores for a leng P along $\vec{s}$ can be calculated as follows:

$$t1_P = Fa + \overline{t1}_{Blk}$$

$$t2_P = Fb + \overline{t2}_{Blk} \tag{11}$$

Where F is a multiplication factor and is defined as:

$$F = \frac{P}{|\vec{s}|}$$

Note that for P we can substitute the lengths Us and Ls in order to determine the corresponding co-ordinates for $U_{s'}$ and $L_{s'}$, respectively, from equation (11). $U_{s'}$ and $L_{s'}$ are calculated as follows:

2. Classification

Once the parameters (Ur, c, d, $\theta_r$, Us'($\alpha$)) and (Lr, c, d, $\theta_r$, Ls' ($\alpha$)) have been determined, the equations representing the upper and lower confidence intervals for the ellipse can be defined. Real data are projected onto the PCA calibration map and compared to the ellipse generated from the calibration data.

The present inventors prefer to utilise the boundary of the ellipse itself as the threshold for classifying a sample as being positive. In other words, if a sample produces a PCA result which lies within the ellipse, it is classified as negative, whereas if a sample produces a PCA result which lies outside tie ellipse, it is classified as positive for BV. However, the skilled reader will appreciate that there are sundry variations in the way in which the threshold might be set. For example, the lower confidence intervals of the ellipse might be used as the threshold.

$$Ls' = \sqrt{\frac{(Lr)^2(Nt1_{Ls} + Mt2_{Ls} - d)^2}{(Lr)^2 - (Mt1_{Ls} - Nt2_{Ls} - c)^2}}$$

3. System Verification $$Us' = \sqrt{\frac{(Ur)^2(Nt1_{Us} + Mt2_{Us} - d)^2}{(Ur)^2 - (Mt1_{Us} - Nt2_{Us} - c)^2}}$$

Calibration standards are run on the system at regular intervals. This process is known as a system verification process. Sensor responses can vary over a period of time, and this response variation is often manifest as a rotation of Std1, Std2, and Std3 responses about the origin of the PCA calibration map. An advantage with the use of an ellipse to define threshold values (as opposed to, for example; a linear threshold on either PC axis) is that such rotation can be accommodated. However, it is possible that sensor drift (or other factors) may cause so large a shift in sensor response that the Std1 and Std3 responses are unacceptably far removed from the ellipse when these responses are transferred onto the PCA calibration map. In this instance, the entire process can be repeated, and a new PCA calibration map generated. A system verification process is now described.

A lower limit ellipse classification boundary (LECB) and an upper limit ellipse classification boundary (UECB) are useful panmeters in conducting system verification checks. The algebraic expression describing the LECS and UECB can be determined by the following sets of parameters, such that:

LECB[Lr(NSr), Ls'(NSs), c, d, $\theta_r$]

UECB[Ur(NSr), U'(NSs), c, d, $\theta_r$]

Note that the parameters c, d, and $\theta_r$ are already calculated. Calculating Lr and Ur Lr and Ur are functions of the NSr parameter which is express in standard deviation units from the mean of the Std1 standard along vector $\vec{r}$.

$$Lr = r - NSr \times sd_r \tag{12}$$

$$Ur = r + NSr \times sd_r \tag{13}$$

Calculating the PC coordinates for lengths Ls and Us along $\vec{s}$.

Ls and Us are both functions of the NSs parameter which is expressed in standard deviation units from the mean of the Std3 standard along vector $\vec{s}$.

$$Ls = s - NSs \times sd_s \quad (14)$$

$$Us = s + NSs \times sd_s \quad (15)$$

$\vec{s}$ can be written in vector notation as:

$$\vec{s} = a\underline{i} + b\underline{j}$$

where $a = \overline{t1}_{Std3} - \overline{t1}_{Blk}$ and $b = \overline{t2}_{Std3} - \overline{t2}_{Blk}$ (See equation 10) The PC1 and PC2 coordinates for the length Ls and Us along vector $\vec{s}$ is calculated as follows:

$$t1_{Ls} = \left(\frac{Ls}{s}\right)a + \overline{t1}_{Blk} \quad (16)$$

$$t2_{Ls} = \left(\frac{Ls}{s}\right)b + \overline{t2}_{Blk} \quad (17)$$

$$t1_{Us} = \left(\frac{Us}{s}\right)a + \overline{t1}_{Blk} \quad (18)$$

$$t2_{Us} = \left(\frac{Us}{s}\right)b + \overline{t2}_{Blk} \quad (19)$$

Calculating Ls' and Us'

$$Ls' = \sqrt{\frac{(Lr)^2(Nt1_{Ls} + Mt2_{Ls} - d)^2}{(Lr)^2 - (Mt1_{Ls} - Nt2_{Ls} - c)^2}} \quad (20)$$

$$Us' = \sqrt{\frac{(Ur)^2(Nt1_{Us} + Mt2_{Us} - d)^2}{(Ur)^2 - (Mt1_{Us} - Nt2_{US} - c)^2}} \quad (21)$$

where values for M and N are as calculated earlier.

The LECB and UECB is used during system verification. In one embodiment, a number of Std1, Std3 and Blk standards are run. Std1 and Std3 standards should produce PCA results which lie within the interval defined by the LECB and UJECB, ie, outside the LECB but inside the UECB. The Blk standards should produce PCA results which lie wit the LECB. An acceptable protocol is to run three Std1, tree Std3 and three Blk, and to require that all of the Blk standards, at least two of the Std1and at least two of the Std3 standards satisfy these criteria. If this is not the case, then the system should be recalibrated. The system verification can be performed at any suitable juncture, such as before a batch of samples is analysed or perhaps on a daily basis.

Variants to the scheme described above would suggest themselves to the skilled reader. For example, samples may be separated and classified using Mahalanobis distance measure. Other forms of data reduction than Principle Components Analysis might be used, such as Sammon Mapping. In principle, more than two principal components might be used to construct the calibration map. Such an approach may not be of great advantage in the context of the technique for detecting BV discussed above. However, the data processing principles discussed above may be applicable to the analysis of gas sensors in other application areas and the approach may even be applicable beyond the field of gas sensors, perhaps to the analysis of data from combinations of other kinds of sensor, or to multiva-rate data analysis per se, In the instance where acetic acid alone is being detected as a "marker" for BV, it may be appropriate to utilise a single PCA axis, i.e., to consider a single principal component. Other forms of data analysis, such as neural networks or chemometric techniques, might be used. It will be appreciated by the skilled reader that, although the calibration map is a useful device for visually displaying the results of calibration and subsequent real data, for the purposes of calculating whether a sample is positive or negative it is not essential to display such a map. Rather, the method of performing data reduction to provide calibration loadings which are used to transform the output of the detector so tat an assessment of whether BV is present can be performed entirely in software, without actually constructing a map per se.

Instead of detecting gaseous and volatile species in the gas phase, it may be possible to perform measurements in the liquid phase. Spectroscopic techniques such as infxa-red spectroscopic might be used. Alternatively, continuous flow methods, electrochemical techniques, or analysis by measurement of electrical impedance, such as described in International Publication No. WO 98/96985, might be contemplated.

Having described and illustrated the principles of the invention in a preferred embodiment thereof, it should be apparent that the invention can be modified in gement and detail without departing from such principles. We claim all modifications d variation coming within the spirit and scope of the following claims.

What is claimed is:

1. A method for detecting the presence of bacterial vaginosis in a female subject comprising the steps of:

obtaining a sample from the vaginal region of the subject;

detecting acetic acid present in the sample; and correlating the presence of detected acetic acid with the presence of bacterial vaginosis.

2. A method according to claim 1 in which acetic acid present as a gas in a headspace associated with the sample is detected using a detector which is sensitive to the presence of acetic acid.

3. A method according to claim 1 in which the sample is a swab sample.

4. A method according to claim 3 in which a high vaginal swab sample is obtained.

5. A method according to claim 1 in which ammonia and, optionally, amine species present in the sample are detected, and the presence of detected acetic acid, ammonia and, optionally, amine species is correlated with the presence of bacterial vaginosis.

6. A method according to claim 1 in which ammonia and, optionally, amine species present as gas in the headspace associated with the sample are detected by the detector.

7. A method according to claim 2 in which the sample is a swab sample.

8. A method according to claim 3 in which a gas sensitive layer.

9. A method according to claim 2 in which the detector comprises semiconducting organic polymer.

10. A method according to claim 2 in which the detector comprises at least one conductimetric gas sensor having a gas sensitive layer onto which gases adsorb and desorp, and in which analytes are detected by:

exposing the gas sensor to the headspace, thereby allowing the adsorption of analytes present in the headspace onto the gas sensitive layer; and making conductimetric measurements of the sensor during a desorption phase in which there is nett desorption of analyte from the gas sensitive layer.

11. A method according to claim 10 in which the conductimetric gas sensor or sensors comprise semiconducting organic polymer.

12. A method according to claim 7 in which:

data reduction of one or more measurements of one or more calibration samples is performed to provide reference scores and reference loadings; and data reduction of the output of the detector performed using the reference loadings.

13. A method according to claim 12 in which the data reduction comprises a principal components analysis.

14. A method according to claim 12 in which the reference scores and reference loadings relate to a co-ordinate system having an axis which is correlated to the presence of acetic acid.

15. A method according to claim 14 in which the reference scores and reference loadings relate to a co-ordinate system having one axis which is correlated to the presence of acetic acid and another axis which is correlated to the presence of ammonia and, optionally, amine species.

16. A method according to claim 12 in which:

the reference scores and reference loadings relate to a co-ordinate system having a species characteristic axis which is correlated to the presence of a species; and data reduction of intensity data from the detector is performed using the reference loadings so that position along the species characteristic axis is related to the concentration in the headspace of the species which is correlated to the species characteristic axis.

* * * * *